(12) United States Patent
Eglitis et al.

(10) Patent No.: US 7,022,321 B2
(45) Date of Patent: Apr. 4, 2006

(54) USE OF MARROW-DERIVED GLIAL PROGENITOR CELLS AS GENE DELIVERY VEHICLES INTO THE CENTRAL NERVOUS SYSTEM

(76) Inventors: Martin A. Eglitis, 8573 Twin Pointe Cir., Indianapolis, IN (US) 46236; Eva Mezey, 6515 Old Farm La., Rockville, MD (US) 20852; Mary Maral Mouradian, 9304 Wildoak Dr., Bethesda, MD (US) 20814

( * ) Notice: Subject to any disclaimer, the term of this patent is extended or adjusted under 35 U.S.C. 154(b) by 450 days.

(21) Appl. No.: 10/122,703

(22) Filed: Apr. 11, 2002
(Under 37 CFR 1.47)

(65) Prior Publication Data

US 2003/0003087 A1 Jan. 2, 2003

Related U.S. Application Data

(63) Continuation-in-part of application No. 09/819,096, filed on Feb. 16, 2001, now abandoned, which is a continuation of application No. 09/058,160, filed on Apr. 10, 1998, now abandoned.

(60) Provisional application No. 60/036,592, filed on Apr. 10, 1997.

(51) Int. Cl.
*A01N 63/00* (2006.01)
*A01N 65/00* (2006.01)
*A61K 48/00* (2006.01)

(52) U.S. Cl. .................. 424/93.21; 424/93.1; 424/93.2

(58) Field of Classification Search ............... 424/93.1, 424/93.2, 93.21
See application file for complete search history.

(56) References Cited

U.S. PATENT DOCUMENTS 5,716,616 A  2/1998  Prockop et al. ............ 424/93.7

FOREIGN PATENT DOCUMENTS

WO     WO 99/43286     9/1999

OTHER PUBLICATIONS

Cao et al. (2002) Stem cell repair of central nervous system injury. Journal of Neuroscience Research 68: 501-510.*
Friedmann, T. (1997) Overcoming the obstacles to gene therapy. Scientific American, Jun. 1997, pp. 96-101.*
Mehler et al. (1999) Progenitor cell biology: Implications for neural regeneration. Archives of Neurology 56(7): 780-784.*
Milward et al. (1997) Isolation and transplantation of multipotential populations of epidermal growth factor-responsive, neural progenitor cells from the canine brain. Journal of Neuroscience Research 50: 862-871.*
Orkin and Motulsky (1965) Report and recommendation of the panel to assess the NIH investment in research on gene therapy pp. 1-38, availabe at http://www.nih.gov/news/panelrep.html.*
Ross et al. Gene therapy in the United States: A five year status report. Human Gene Therapy 7: 1781-1790.*
Rossi and Cattaneo (2002) Neural stem cell therapy for neurological diseases: dreams and reality. Nature Reviews Neuroscience 3: 401-409.*
Rubanyi, GM (2001) The future of human gene therapy. Molecular Aspects of Medicine 22: 113-142.*
Verma et al. (1997) Gene therapy—promises, problems and prospects. Nature 389: 239-242.*
Altman, J., *TINS* 17(2):47-49, 1994.
Banati et al., "A Subpopulation of Bone Marrow-Derived Macrophage-Like Cells Shares a Unique Ion Channel Pattern with Microglia," *J. Neuroscience Research* 30(4): 593-600, Dec. 1991, Abstract only.
Brazelton, T.R., et al., "From Marrow to Brain: Expression of Neuronal Phenotypes in Adult Mice," *Science* 290:1775-1779, 2000.
Eglitis et al., "Contribution of Bone Marrow-Derived Cells to Lesion-Associated Gliosis in the Adult CNS," *Soc. Neurosci. Abstr.* 22:1691, 1997. Abstract.

(Continued)

*Primary Examiner*—Anne-Marie Falk
(74) *Attorney, Agent, or Firm*—Klarquist Sparkman, LLP

(57) ABSTRACT

The present disclosure relates to a method for introducing a hematopoietic cell into the brain of a mammal, by administering bone marrow-derived progenitor cells into the body of the mammal by intravenous injection. The bone marrow-derived cell is preferably a cell that differentiates into a glial cell.

The disclosure also relates to a method for delivery of therapeutic protein molecules into the brain of a mammal, by administering to a mammal an effective amount of bone marrow-derived progenitor cells which contain a gene having a nucleic acid sequence that encodes a functional therapeutic protein.

Isolated recombinant cells and a pharmaceutical composition are also provided.

8 Claims, 3 Drawing Sheets

OTHER PUBLICATIONS

Eglitis et al., "Ex Vivo GDNF Gene Transfer Using Marrow Cells in Rodent Models of Dopaminergic Neurodegeneration," *Soc. Neurosci. Abstr.* 24:1222, 1998. Abstract.

Eglitis et al., "Hematopoietic Cells Differentiate Into Both Microglia and Macroglia in the Brains of Adult Mice," *Proc. Natl. Acad. Sci. USA* 94:4080-4085, Apr. 1997.

Eglitis et al., "Targeting of Marrow-Derived Astrocytes to the Ischemic Brain," *NeuroReport* 10:1289, 1999.

Fedoroff, S., "Development of Microglia," in *Neuroglia*, eds. Kettenmann, H. & Ransom, B. R. (Oxford University Press, New York), pp. 162-181, 1995.

Learish et al., "Retroviral Gene Transfer and Sustained Expression of Human Arylsulfatase A," *Gene Therapy* 3(4):343-349, Apr. 1996.

Lewis, P. D., "The Fate of the Subependymal Cell in the Adult Rat Brain, with a Note on the Origin of Microglia," *Brain.* 91:721-738, 1968.

Ling, E.-A. and Wong, W.-C., "The Origin and Nature of Ramified and Amoeboid Microglia: A Historical Review and Current Concepts," *Glia.* 7:9-18, 1993.

Kitamura, T., Miyake, T. & Fujita, S., "Genesis of Resting Microglia in the Gray Matter of Mouse Hippocampus," *J. Comp. Neurol.* 226:421-433, 1984.

Krall, W.J., et al., "Cells Expressing Human Glucocerebrosidase From a Retroviral Vector Repopulate Macrophages and Central Nervous System Microglia After Murine Bone Marrow Transplantation," *Blood* 83(9):2737-2748, 1994.

Maréchal, V., et al., "Disappearance of Lysosomal Storage in Spleen and Liver of Mucopolysaccharidosis VII Mice After Transplantation of Genetically Modified Bone Marrow Cells," *Blood* 82(4):1358-1365, 1993.

Mezey, E., et al., "Turning Blood into Brain: Cells Bearing Neuronal Antigens Generated In Vivo from Bone Marrow," *Science* 290:1779-1782, 2000.

Mouradian, M.M., et al., "Protection of Nigral Neurons by GDNF-Engineered Marrow Cell Transplantation in the Mouse MPTP Model," *Mov. Disord.* 15(Suppl. 3):15, 2000. Abstract.

Neuhaus, J. & Fedoroff, S., "Development of Microglia in Mouse Neopallial Cell Cultures," *Glia.* 11:11-17, 1994.

Park, K-W, et al., "Protection of Nigral Neurons by GDNF-Engineered Marrow Cell Transplantation," *Neuroscience Research* 40:315-323, 2001.

Perry, V. H. & Gordon, S., "Macrophages and Microglia in the Nervous System," *TINS* 11(6):273-278, 1988.

Skoff, R. P. & Knapp, P. E., "The Origins and Lineages of Macroglial Cells," in *Neuroglia*, eds. Kettenmann, H. & Ransom, B. R. (Oxford University Press, New York), pp. 135-148, 1995.

Snyder et al., "The Use of Nonneuronal Cells for Gene Delivery," *Neurobiol. Dis.* 4(2):69-102, 1997.

Theele, D. P. & Streit, W. J., "A Chronicle of Microglial Ontogency," *Glia.* 7:5-8, 1993.

Unger, E.R., et al., "Male Donor-Derived Cells in the Brains of Female Sex-Mismatched Bone Marrow Transplant Recipients: A Y-Chromosome Specific *In Situ* Hybridization Study," *Journal of Neuropathology and Experimental Neurology* 52(5):460-470, 1993.

Zlokovic, B.V., et al., "Cellular and Molecular Neurosurgery: Pathways From Concept to Reality—Part I: Target Disorders and Concept Approaches to Gene Therapy of the Central Nervous System," *Neurosurgery* 40(4):789-804, Apr. 1997.

Zlokovic, B.V., et al., "Cellular and Molecular Neurosurgery: Pathways From Concept to Reality—Part II: Vector Systems and Delivery Methodologies for Gene Therapy of the Central Nervous System," *Neurosurgery* 40(4):805-813, Apr. 1997.

* cited by examiner

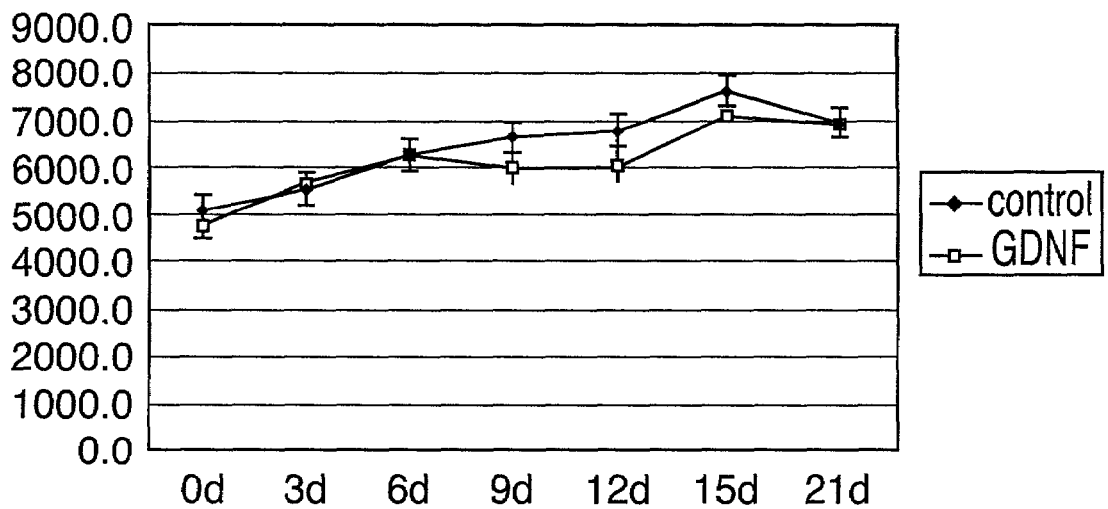
FIG. 3A  Horizontal activity
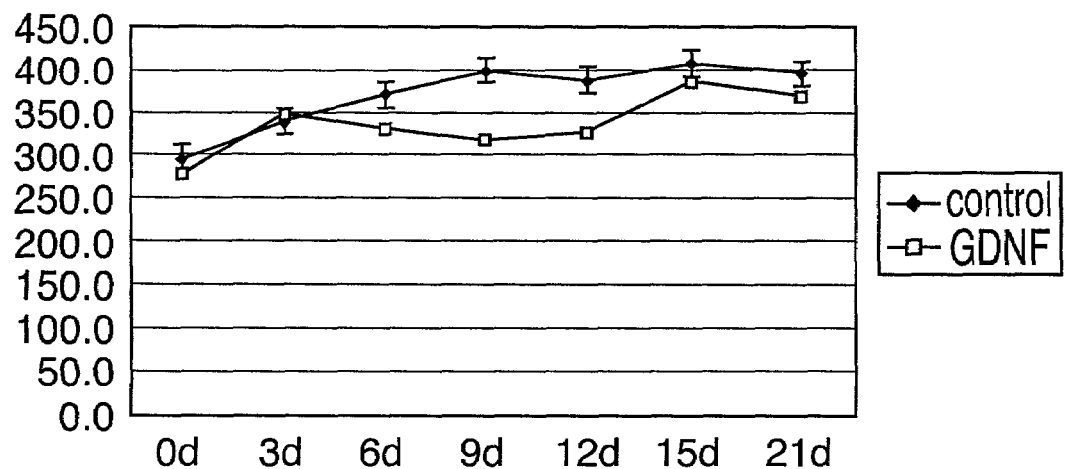
FIG. 3B  Number of Movements

USE OF MARROW-DERIVED GLIAL PROGENITOR CELLS AS GENE DELIVERY VEHICLES INTO THE CENTRAL NERVOUS SYSTEM

REFERENCE TO RELATED APPLICATIONS

This is a Continuation in Part of U.S. application Ser. No. 09/819,096, filed Feb. 16, 2001, now abandoned, which was a Continuation of U.S. application Ser. No. 09/058,160, filed Apr. 10, 1998, now abandoned, which claimed the benefit of U.S. Provisional Application No. 60/036,592 filed Apr. 10, 1997.

FIELD

The present disclosure relates to methods for introducing hematopoietic cells into the brain of a mammal, the differentiation of adult bone marrow cells into glial cells, and the use of marrow-derived glial progenitor cells as gene delivery vehicles into the brain.

BACKGROUND

Glial cells are thought to derive embryologically from either myeloid cells of the hematopoietic system (microglia) or neuroepithelial progenitor cells (astroglia and oligodendrocytes). However, it is unclear whether the glia in adult brains free of disease or injury originate solely from cells present in the brain since the fetal stage of development, or if there is further input into such adult brains from cells originating outside the central nervous system (CNS).

Besides the cells of the vasculature, the brain comprises two general cell types: neurons and glial cells. Glial cells provide physiological support to neurons and repair neuronal damage due to injury or disease. Macroglia (astroglia and oligodendroglia) are generally considered to be derived from neuro-ectoderm and are believed to be developmentally distinct from microglia (1). However, the developmental origin of microglia remains debatable (2,3). The two major views are that they derive either from neuro-epithelial cells (4–6) or from hematopoietic cells (i.e., monocytes) (7,8). The extent to which cells outside the CNS contribute to the maintenance of microglia in adults remains debatable (compare (9) and (10)), and no such contribution to adult neurons or macroglia has been previously described.

SUMMARY OF THE DISCLOSURE

Heretofore, gene therapy in the brain relied upon surgically implanting the transfected cells into the recipient brain. It was unknown prior to our disclosure that cells of the hematopoietic system are a source of progenitor cells for the CNS, such that these cells can be used as a gene therapy delivery vehicle into the brain.

We tested the ability of hematopoietic cells to contribute to the CNS, by transplanting adult female mice with donor bone marrow cells genetically marked either with a retroviral tag or by using male donor cells. We monitored the appearance of the cells in the brain using in situ hybridization histochemistry (ISHH) combined with immunohistochemistry. We also performed double ISHH with digoxigenin and radioactively labeled probes to analyze which cell types might be derived from bone marrow stem cells. We detected a continuing influx of hematopoietic cells into the brain. Marrow-derived cells were already detected in the brains of mice three days after transplant and their numbers increased over the next several weeks, exceeding 14,000 cells per brain in several animals. Marrow-derived cells were widely distributed throughout the brain, including the cortex, hippocampus, thalamus, brainstem, and cerebellum. When ISHH was combined with immunohistochemical staining using lineage-specific markers, some bone marrow-derived cells were positive for the microglial antigenic marker F4/80. Other marrow-derived cells surprisingly expressed the astroglial marker glial fibrillary acidic protein (GFAP). These results indicate that some microglia and astroglia arise from a precursor that is a normal constituent of adult bone marrow.

The results reported here confirm that cells derived from the bone marrow can migrate into the brains of adult mice. Furthermore, we have found that this migration is rapid, with numerous cells present by the third day after transplant. These new cells are distributed throughout the brain, and appear to reside within the parenchyma, since perfusion with PBS does not remove them. Occasional donor marrow-derived cells were found in association with vascular structures. Moreover, densities of donor cells in the parenchyma paralleled the capillary density of a given region. For instance, cortex, with fewer capillaries, had a lower cell density than the more vascularized choroid plexus. Regions with a higher capillary density, such as the area postrema, also had the highest density of marrow-derived cells within the parenchyma.

Double-labeling analyses show that at least some bone marrow-derived cells acquire microglial antigenic markers. However, we also observed many cells positively labeled by ISHH that did not express the F4/80 antigen. This may be due simply to a level of antigen below the limits of detection in our assay.

Alternatively, it is possible that the F4/80 marker is expressed on marrow-derived cells only after they fully differentiate into microglia, while less mature microglial precursors are not recognized by the antibody to F4/80. Nonetheless, our results strongly support the view that hematopoietic cells outside the CNS contribute to the maintenance of microglia in healthy adults. While a partial CNS origin of adult microglia cannot be excluded, our data is inconsistent with an exclusively CNS origin. Moreover, although our experiments did not examine fetal origins of microglia, the finding of hematopoietically-derived microglia in healthy adults is also consistent with a hematopoietic origin of microglia in development.

Surprisingly, we found that some hematopoietic cells (tagged either with a retroviral vector or by transplant of male cells into a female recipient) give rise to cells other than microglia, specifically to cells that exhibit astroglial markers. Although this observation is unexpected, it is based on identical results in multiple animals using two independent means of cell tagging with both cytoplasmic and nuclear markers.

The appearance of marrow-derived astroglia seems a normal process in these animals. Because the number of marrow-derived cells detected in the brain increased over time, their appearance does not appear to be a consequence of the transplantation procedure itself. If appearance in the brain was a by-product of transplantation, one would expect tagged cell numbers in the brain to peak and then decline, which was not observed. Rather, the data is consistent with existence of cells, amongst the populations of marrow-engrafting cells, capable of continuous generation of progenitors that migrated to the brain. Interestingly, cells with marrow markers were seen in the ventricular ependyma. In fact, in many animals, marrow-derived cells could be found concentrated sub-ependymally (Mezey & Eglitis, in preparation). The subependymal zone is an important source of neuronal and glial progenitors during development (24) and in adults (27). Finding bone-marrow derived cells in this location opens the possibility that such cells receive cues guiding their differentiation once they enter the brain. Studies evaluating this possibility are ongoing.

No obvious pathology such as gliosis was detected in the brain of any transplant recipient (n=46). Some recipient animals were irradiated before receiving bone marrow transplants to see if marrow purging enhanced engraftment and seeding of implanted cells. However, radiation dosages were at least one order of magnitude below those known to induce pathological changes in the CNS (29). Indeed, we found preconditioning of recipients was not necessary. Male donor cells engrafted and persisted for at least 10 weeks even without irradiation. Furthermore, as many Y chromosome/GFAP double positive cells were seen with as without irradiation. The wide distribution of GFAP-positive cells in both gray and white matter demonstrates that bone marrow-derived progenitors are not restricted to differentiate into a particular subclass of astroglia. That is, marrow-marked cells contributed to both fibrous astrocytes in the white matter and protoplasmic astrocytes in the gray matter.

One alternative explanation for our observing GFAP staining of cells bearing marrow markers is that processes from endogenous astroglia surround the in-migrating cells from the donor marrow. However, some of our data argue against this possibility. First, cytoplasmic $neo^R$ ISHH labeling coincided with cytoplasmic GFAP immunostaining. Furthermore, upon evaluation of fifty to 100 male nuclei associated with GFAP staining, no nuclei were seen that could be considered part of an engulfing astroglial cell. If endogenous astroglia were the source of the GFAP staining associated with donor male nuclei, one would expect the geometry in 12µ sections to reveal the cell body and nucleus corresponding to the putative engulfing processes in at least a few cases. After analyzing dozens of sections, no such cases were observed.

Because only about 10% of marrow-derived cells in the brain exhibit expression of either the microglial F4/80 antigen or the astroglial marker GFAP, the identity of the majority of bone marrow-derived cells remains an open question. Nonetheless, there is clearly a measurable contribution by cells of hematopoietic origin to the glial cell population of the brain in adult mice, which indicates that some glial progenitors reside outside the CNS. The observation of marrow-derived astroglia in the optic tract demonstrates that some of these marrow-derived progenitors may be similar to the previously recognized astroglial precursor (30).

Microglia and astroglia respond differently to brain injury. In fact, astrogliosis often appears to be a response to primary microgliosis (31,32). There is also evidence that different brain lesions elicit different microglial and astroglial responses (33). Our results provide a way that gene transfer into hematopoietic progenitors can be used to introduce genes into microglia and astroglia that then would participate in the gliosis associated with a CNS pathology. The detection of marrow-derived cells in brains within days of transplantation provides a method in which genetically altered hematopoietic cells could be used to treat acute diseases of the brain.

Although many neurotrophic factors show promise in the treatment of CNS disorders, their use has been hindered by their inability to cross the blood-brain barrier and by their limited diffusion into CNS tissues (34). In addition, adverse effects have been reported after systemic administration of some neurotrophins (35). Using marrow-derived cells to deliver therapeutic proteins directly to the site of CNS pathology likely would be more benign than systemic administration of toxic molecules. In addition, using vectors with cell type-specific promoters could restrict gene expression specifically to reactive astroglia or microglia, thereby providing greater therapeutic precision for gene therapy of CNS disease.

BRIEF DESCRIPTION OF THE FIGURES

FIG. 3 shows the effect of transplantation with genetically engineered marrow cells in a mouse model of Parkinson's disease described in Experiment 10. FIG. 3A is a graph of horizontal activity versus time. FIG. 3B is a graph of the number of movements versus time.

DETAILED DESCRIPTION

Figure 1:
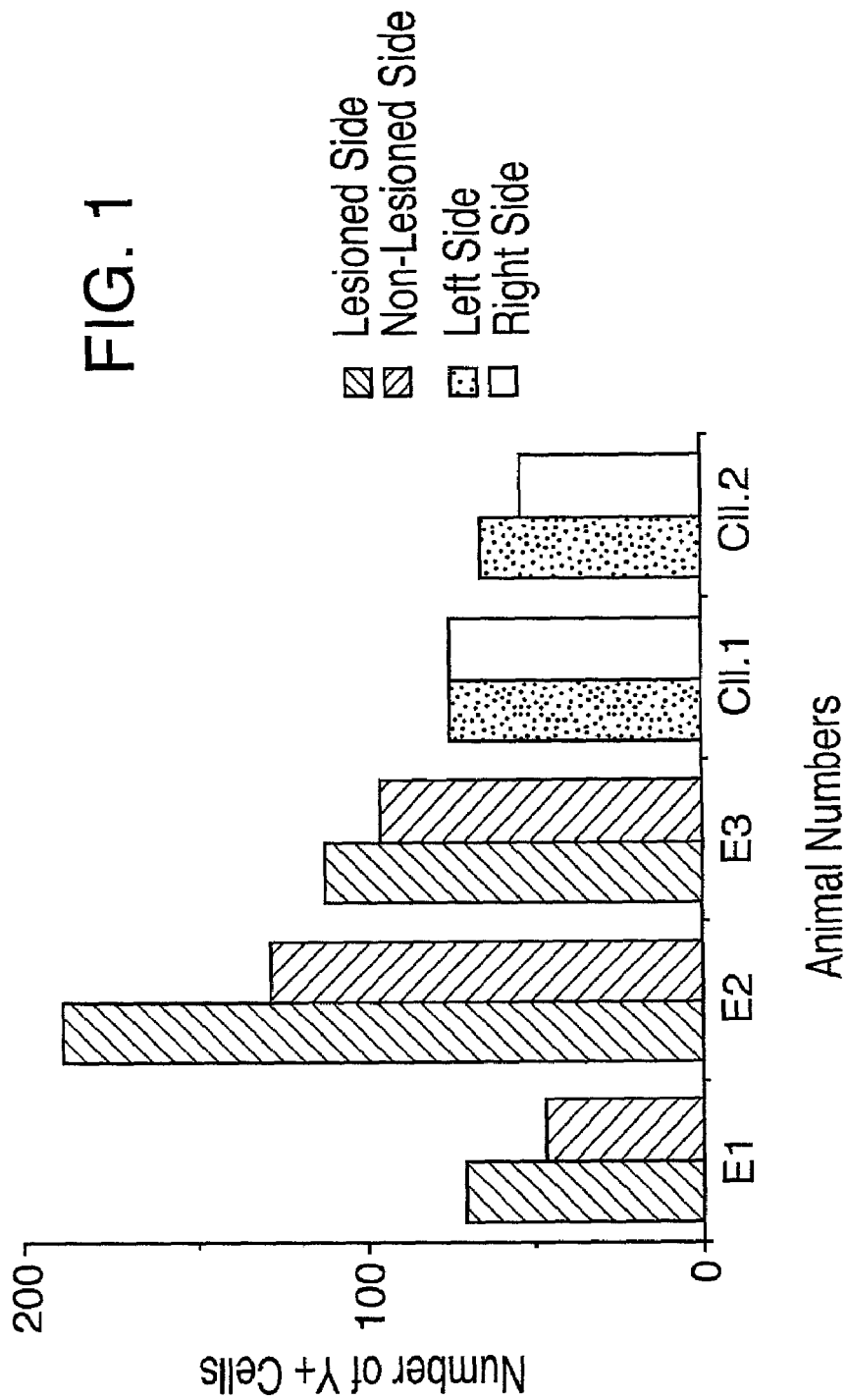
FIG. 1 shows the behavior of marrow-derived glia in the rat ischemic injury model described in Experiment 9. Shown is the number of marrow-derived cells detected in the lesioned ischemic vs. the contralateral non-ischemic side of three rat cortexes following MCA occlusion using Y chromosome-specific hybridization.

Experiment 1: Gene Transfer and Bone Marrow Transplantation

Gene transfer into hematopoietic precursors was done as previously described (11,12), with the addition of stem cell factor to optimize transduction of reconstituting hematopoietic stem cells (13). C57BL/6J mice (Jackson Laboratories, Bar Harbor, Me.), 6–8 weeks old, were used as donors. Forty-eight hours before marrow harvest, the mice were injected with 5-fluorouracil at a dose of 150 mg/kg to ablate mature blood cells and thereby induce progenitor cells into cycle. Upon harvest, marrow was placed into liquid culture in suspension dishes and grown in Dulbecco's modified Eagle's medium containing 15% fetal bovine serum (Whittaker Bioproducts, Walkersville, Md.) and supplemented with IL-3 (50 ng/ml), IL-6 (100 ng/ml) and stem cell factor (100 ng/ml). Growth factors were used to maintain early hematopoietic cells in cycle (13). All were obtained from R & D Systems (Minneapolis, Minn.). After 48 hr in culture with growth factors, marrow cells were collected and added to tissue culture dishes containing the F5B producer cell line at subconfluent density. F5B cells shed the N2 retroviral vector, packaged with the ecotropic envelope and carrying the bacterial gene for neomycin resistance ($neo^R$) (14). Following 48 hr co-culture with F5B cells, bone marrow cells were collected by gentle aspiration, suspended to $1\times10^7$ cells/ml in phosphate buffered saline (PBS, in all cases 0.1 M phosphate, 140 mM NaCl, pH 7.6) and injected intravenously ($2-3\times10^6$ cells/mouse) via the tail vein into sub-lethally irradiated (4.5 Gy) female WBB6F1/J-$Kit^W/Kit^{W-v}$ mice. WBB6F1/J-$Kit^W/Kit^{w-v}$ mice are particularly good recipients for bone marrow transplantation because they have genetically defective stem cells (15). This gives normal C57BL/6J donor stem cells a strong repopulating advantage.

In transplants of male donor marrow into female recipients, some marrow was marked with retroviral vector as described. In other cases, marrow was harvested, washed with PBS, and transplanted directly into recipient mice without culturing in growth factor-containing medium or irradiation of recipient animals.

A total of 46 mice were transplanted, 38 with vector tagged marrow and 8 with male marrow. Five of the transplants with vector tagged marrow used male donor cells. Mice were sacrificed at various times after transplantation. At least two animals were analyzed at each time point, although more were used at the 14 day (n=10), 35 day (n=14), and 70 day (n=6) time points. Tissues were collected and immediately frozen on dry ice for subsequent sectioning. Some animals underwent cardiac perfusion with PBS before tissue harvest. Animals for perfusion were anesthetized with carbon dioxide, then their chest was opened and PBS was introduced through a cannula placed in the left ventricle. The left atrium was incised to allow release of blood. Animals were perfused with 50 ml of ice cold PBS over a period of 5 min.

Experiment 2: In situ Hybridization Histochemistry

Tissues were evaluated with both oligonucleotide and RNA probes. To detect $neo^R$ transcripts, two oligonucleotide probes were prepared, complementary to the sequence of the $neo^R$ gene either from nucleotides 222–269 or from nucleotides 447–494 (numbering with the A of the initiation codon as 1). The oligonucleotides were labeled using terminal transferase (Boehringer-Mannheim, Indianapolis, Ind.) and $^{35}$S-dATP (New England Nuclear, Boston, Mass.) as described previously (16). An RNA probe, complementary to the entire $neo^R$ coding region, was labeled with $^{35}$S-UTP using SP6 polymerase (17). Labeling with radioactive probes was detected by dipping hybridized sections in photographic emulsion. Emulsion was exposed for 14 days, then developed and sections were stained, air dried, and coverslipped for microscopic examination. To detect male bone marrow cells transplanted into female recipients, sequences specific to the donor mouse Y chromosome were detected using a complementary RNA probe derived from the plasmid pY353/b (18). GFAP gene expression was detected using an RNA probe complementary to the entire GFAP coding region. The Y chromosome and GFAP probes were labeled using digoxigenin-UTP (19), and digoxigenin labeling was developed for GFAP using alkaline phosphatase as described (19). For detection of the donor Y chromosome, before overnight hybridization with digoxigenin-labeled probes at 55° C., the slides were heated at 90° C. for 10 minutes in hybridization buffer containing the probes to improve access to nuclear DNA. The digoxigenin-labeled Y chromosome was visualized using a modification (Mezey et al., in preparation) of an immuno-staining amplification method (20), which results in green fluorescein isothiocyanate (FITC) fluorescence.

Twelve-micron thick frozen sections were cut in a cryostat and ISHH was performed as described previously (16,17). The sections were fixed, dehydrated, and delipidated in ethanol and chloroform and then hybridization buffer containing the probe(s) was put on the sections. Slides were incubated overnight in a humidified chamber at 37° C. (for oligonucleotide probes) or 55° C. (for riboprobes).

Experiment 3: Nuclear Staining

To confirm that Y chromosome ISHH coincided with cell nuclei, sections were counterstained with ethidium bromide or 4',6-diamidino-2-phenylindole (DAPI). Staining was detected by illumination with a mercury lamp using a microscope equipped for fluorescence micrography.

Experiment 4: Immunohistochemical Analysis

For combined ISHH/immunohistochemical analysis, sections were fixed as described previously (21). They were then incubated for 30 minutes at room temperature in 3% normal goat serum diluted in PBS (containing 0.6% Triton-X 100) to block nonspecific binding. Then, the sections were exposed for one hour at room temperature to either 1) a polyclonal rabbit antibody that detects the mouse F4/80 monocyte/macrophage marker (22) or 2) a polyclonal rabbit antibody against the astroglial marker GFAP (Sigma, St. Louis, Mo.) used at a dilution of 1:2000. Binding of non-labeled primary antisera was detected with either a biotinylated or goat anti-rabbit IgG (Jackson ImmunoResearch Laboratories, Inc., West Grove, Pa.), both diluted 1:500. To detect biotinylated secondary antibody, the sections were incubated for one hour in an avidin-biotin-peroxidase complex diluted 1:250 in PBS with 0.6% Triton-X 100 (23). The slides were then transferred into 0.1 M Tris-HCl (pH 7.6) and were developed using diaminobenzidine as a substrate. Following a thorough wash, the sections were processed for ISHH. Co-labeling of cells was determined using a combination of bright-field, polarized, fluorescent, and epi-illumination microscopy. Controls for the immunostaining included leaving out the primary antibodies and using several secondary antibodies (from different species) to confirm that there was no nonspecific binding.

Experiment 5: Detection of Donor Cells in the Brain After Bone Marrow Transplantation To evaluate the appearance and distribution of donor cells in the brains of recipient mice, animals were sacrificed 3, 5, 7, 14, 28, 35, 42 and 70 days after transplantation with bone marrow cells. At least two animals transplanted with retrovirally tagged marrow were studied at each time point. Mice transplanted with male marrow were analyzed at 35 days (n=9) and 70 days (n=4) after transplantation. Using probes specific to the vector $neo^R$ transcripts, donor cells were detected beginning with day three, the earliest time of analysis. Many cells were easily detected throughout the brain by day seven and cells continued to be detected at all subsequent times. To estimate total number of $neo^R$-positive cells in a brain, every 25th section was collected and all labeled cells in the sections were counted. The number of labeled cells was multiplied by 25 to arrive at the approximate total number of marked cells in a brain. These calculations showed that the overall number of marrow-derived cells per brain gradually increased with increasing time after transplantation. Three days after transplant, 500 cells were detected per brain. Two to 4 weeks after transplant the number of cells present had increased to at least 2000 per brain. In several animals more than 10,000 cells per brain were seen, and in one animal the number of cells was over 30,000.

At one week, and occasionally at later times, concentrations of $neo^R$-marked cells were observed in the basal subarachnoid space. Bright- and dark-field photographs were taken of the same section 14 days post-bone marrow transplantation, and cells marked by the retroviral vector (cells positive by ISHH with $^{35}$S-labeled oligonucleotide or riboprobe) were detected in the hippocampus, septum, hypothalamus, and within the ependyma of the third ventricle. Cells were also detected, among other regions, in the cortex, habenula, pons and cerebellum. Labeled cells were detected after PBS perfusion, indicating that bone marrow-derived cells were an integral part of the brain parenchyma. Double exposures of a brightfield image with a darkfield image were made of the same area. The darkfield image was photographed using a red filter so that the autoradiographic grains would appear red.

Similar regional distribution of donor marrow cells was seen using the Y chromosome probe to detect male donor cells. Donor cells (cells positive for the Y chromosome by ISHH) were detected in several brain regions of a female recipient six weeks after transplantation with male bone marrow cells. Photomicrographs were made of a section through the ventral mesencephalon using a rhodamine filter to excite ethidium bromide staining of the nucleus, a FITC filter to excite Y chromosome-specific FITC staining, and/or a double pass filter to show overlap of Y chromosome labeling and nucleus-specific ethidium bromide staining.

Ethidium bromide counter-staining (to highlight the nucleus) confirmed the nuclear localization of the Y chromosome probe. Many male donor-derived cells were easily detected throughout the brain 35 days after transplantation and cells continued to be detected at all subsequent times. Cells positive for the Y chromosome marker were detected in the mesencephalon, septum, striatum, and habenula. Cells were also detected in the cortex, pons, and cerebellum, among other regions (data not shown). Ex vivo manipulation of the bone marrow cells was not necessary, because male cells were detected in female recipients' brains even when the transplant was done immediately after marrow harvest.

Several parameters were used to verify that the labeling observed after ISHH was specific. First, no labeling was detected in any tissues of animals transplanted with non-marked bone marrow cells. That is, without retroviral tagging, probes for the $neo^R$ gene exhibited no background labeling, and the Y chromosome probe did not label female tissues. With the Y chromosome riboprobe, we also confirmed that both sense and antisense probes exhibited the same distribution, as expected when hybridizing to chromosomal DNA. The pattern of retrovirally-labeled cells was identical in all tissues analyzed, both qualitatively and quantitatively, regardless of which probe was used. Finally, we found donor cells in hematologic organs such as bone marrow and spleen at all time points analyzed. The pattern of engraftment was qualitatively similar between retrovirally tagged and male donor cells. However, when female mice were transplanted with retrovirally tagged male marrow, more donor cells were detected with the Y chromosome probe than with the $neo^R$ probe. Hence, not all of the cells migrating from the bone marrow into the brain expressed the retrovirally introduced $neo^R$ gene at a level high enough to be detected by ISHH.

Experiment 6: Labeling of Brain Sections after ISHH with the Microglial Marker F4/80

The F4/80 detects the plasma membrane protein F4/80 expressed exclusively on macrophages and microglia (22). Co-localization in brain sections (cells co-expressing the microglial marker F4/80 and the $neo^R$ retroviral tag) revealed cells labeled by the N2 retroviral vector that also expressed the F4/80 antigen, confirming that bone marrow-derived cells do contribute to the microglial population in the adult brain. However, only a small percentage of ISHH-positive cells were labeled by immunostaining. Similarly, the minority of antigen-positive cells was doubly labeled by ISHH. The distribution of doubly labeled cells reflected the distribution of cells labeled only by ISHH or by immunohistochemistry, i.e., they were widely distributed throughout the brain.

The F4/80 monocyte/macrophage antigen was detected by indirect immunofluorescent antibody labeling, and $^{35}$S-radiolabeled probes were used to hybridize to $neo^R$ mRNA. Photomicrographs were made of a representative field from an animal sacrificed 35 days after bone marrow transplantation. In one representative photomicrograph, a cell in the center stained positive for the F4/80 antigen (red) and exhibited labeling with radioactive probe to $neo^R$ transcripts. Darkfield images were photographed using a green filter so that autoradiographic grains would appear green (yellow where they overlap red immunostaining).

Experiment 7: Labeling of Brain Sections for Both the Astroglial Marker GFAP and the $neo^R$ Retroviral or Y Chromosome Donor Cell Tag The ISHH-positive, F4/80 negative cells could be cells of the myeloid lineage that had not differentiated to express the F4/80 antigen. Or, they could represent a contribution of bone marrow-derived cells to other than myeloid cell lineages. To distinguish between these alternative possibilities, ISHH-positive cells were examined for the expression of another lineage marker, GFAP, specific for astroglia. Surprisingly, we found occasional cells that were labeled both by ISHH (for the donor marrow $neo^R$ marker) and by indirect immunohistochemistry (for GFAP). Photomicrographs were made of cells within the optic tract expressing GFAP protein using peroxidase-based immunohistochemical staining combined with ISHH to detect expression of $neo^R$ transcripts. Double labeled cells were identified adjacent to clusters of grains indicative of $neo^R$-marked cells that did not express GFAP and GFAP-positive cells that were not marked with the retroviral tag. Counting all of the donor cells present in every 25th section obtained from recipient mice four weeks after transplantation (n=3), we calculated that as many as $3 \times 10^4$ $neo^R$-marked donor cells were present per brain. Of that total donor cell number, we estimated between 0.5% and 2% exhibited GFAP expression.

To confirm that GFAP mRNA was present in some $neo^R$-positive cells, we also did double ISHH analysis. Cells co-expressing GFAP and $neo^R$ mRNAs were identified using a digoxigenin-labeled riboprobe against GFAP mRNA together with a $^{35}$S-labeled probe for the $neo^R$ gene marking the donor marrow. Photomicrographs were made of sections through the cerebral cortex. Polarized epifluorescent illumination was used to emphasize grains indicative of hybridization with $^{35}$S-labeled probe for $neo^R$. Brightfield illumination was used to emphasize digoxigenin staining of GFAP transcripts. We found cells labeled with both probes. Their frequency was approximately equal to the frequency of the ISHH/GFAP immunostained double cells.

We also found doubly labeled cells in multiple animals when ISHH (which was used to detect male cells with the Y chromosome marker) was combined with immunohistochemistry (to detect GFAP protein). Using DAPI staining to highlight the nucleus and three-channel photomicrography, we confirmed that the Y-chromosome ISHH was associated with the nuclei of GFAP-positive cells. Photomicrographs were made of double-labeled cells found in the brains of female recipient mice 10 weeks after bone marrow transplantation. Male donor cells were detected with a Y chromosome-specific riboprobe as described above. Astroglia were identified using a CY3-labeled polyclonal antibody against the astroglial marker GFAP. In particular, sections were made through the cortex, through the septum, and through the corpus callosum. Some sections were illuminated with ultraviolet light to excite DAPI fluorescent staining of the nucleus. Nuclei from all cells were stained. Some sections were illuminated to excite FITC staining of the Y chromosome. Some sections were illuminated to excite CY3-immunostaining of GFAP.

Photomicrographs were also made of single fields from sections through the amygdala. In some photomicrographs, green FITC staining was used to detect the Y chromosome. In other sections, red GFAP immunostaining was photographed, while still other photomicrographs were double exposures of the same field, first with a double band pass filter to excite FITC and CY3 fluorescence, then with ultraviolet illumination to excite the blue DAPI fluorescent staining of the nucleus.

Dark- and bright-field photographs (of the same section) were also made that showed several cells exhibiting labeling for the Y chromosome marker in the fronto/polar cortex of an animal six weeks after bone marrow transplantation are indicated.

Experiment 8: Detection of neo$^R$-Marked Cells in the Brain After Bone Marrow Transplantation with Retrovirally-Marked Bone Marrow Neo$^R$-marked cells were detected in the brain after bone marrow transplantation with retrovirally-marked bone marrow. Photomicrographs were made of representative cells positive for neo$^R$ transcripts visualized by in situ hybridization histochemistry (ISHH). Positive cells were found in the region of the third ventricle of hypothalmus (Hth) of animals sacrificed 35 days after bone marrow transplantation. ISHH-positive cells were found within the arcuate nucleus of animals sacrificed 14 days post-bone marrow transplantation. In addition, ISHH-positive cells were detected in animals 14 days post-bone marrow transplantation.

In addition, bright and darkfield photographs were made of the same field in several of the animals. These photomicrographs showed cells exhibiting labeling for neo$^R$ transcripts in the hippocampus of animals two weeks after bone marrow transplantation (CA3–CA3 region of the hippocampus).

Experiment 9: Behavior of Marrow-derived Glia in a Rat Ischemic Injury Model

Acute cortical ischemia was induced in spontaneously hypertensive (SHR) rats as follows: Under halothane anesthesia, the left middle cerebral artery was exposed using a subtemporal approach (36), and permanently occluded by electrocoagulation midway between the inferior cerebral vein and lateral olfactory tract. Forty-eight hours after surgery, animals were sacrificed and their brains were collected for analysis.

Y chromosome-specific hybridization indicating marrow-derived cells in the cortex of brains of transplanted rats was quantified. The graph in FIG. 1 compares the number of such cells detected in the lesioned ischemic vs. the contralateral non-ischemic side of three animals following MCA occlusion. In addition, the number of marrow-derived cells was compared between the two hemispheres of two intact animals. Statistical analysis of 10 brain sections from the lesioned animals using the Wilcoxon Signed Rank test revealed a significantly higher number of Y+ nuclei on the ischemic side compared with the contralateral non-ischemic cortex (p=0.038). On the other hand, no such difference was found between the two hemispheres in seven sections obtained from intact animals (p>0.1).

Figure 2:
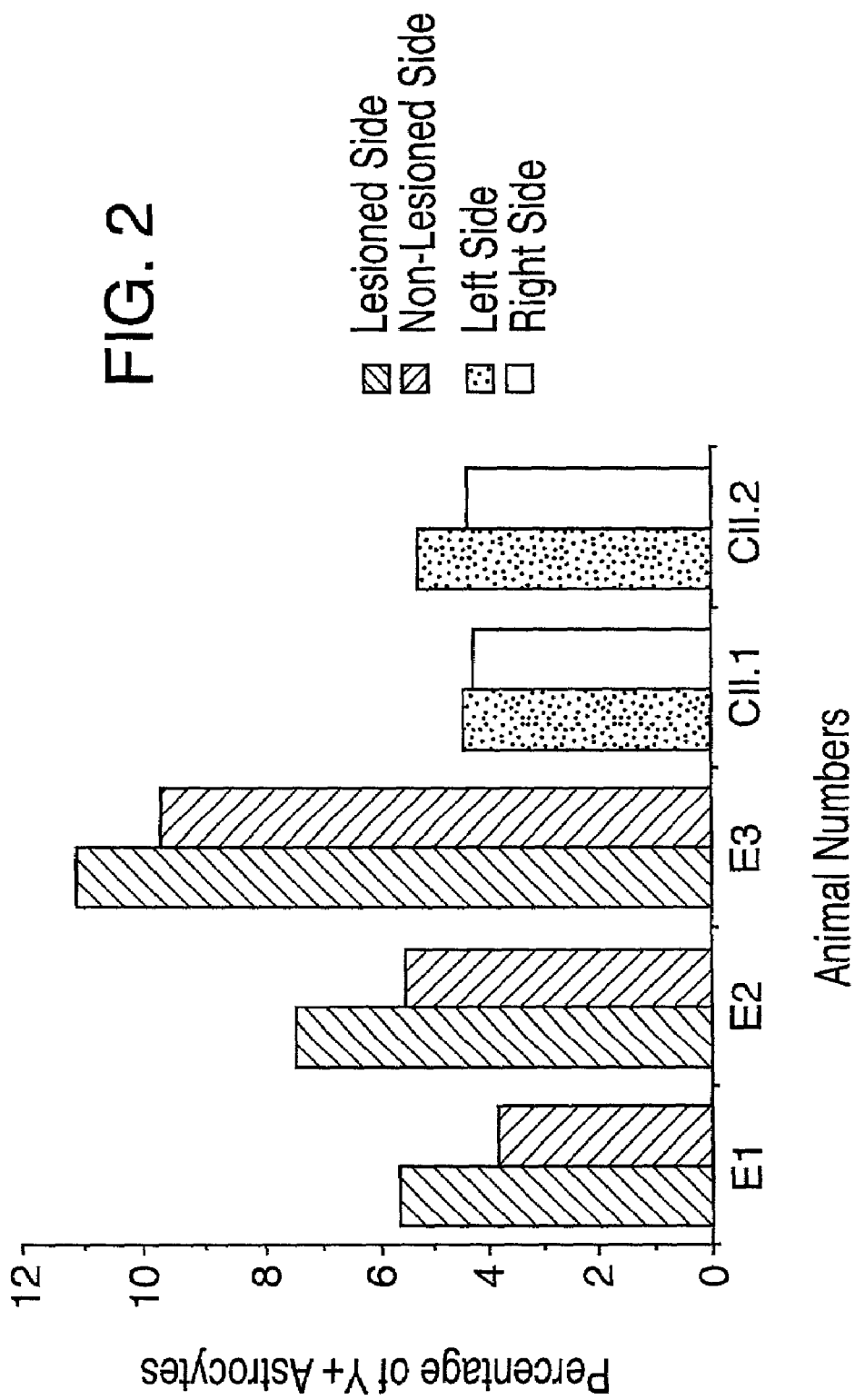
FIG. 2 shows the results of Experiment 9, in that in each of the three lesioned animals, more male donor marrow-derived astrocytes were detected on the ischemic side than on the non-ischemic side.

The number of Y chromosome-positive astrocytes was determined in three lesioned and two intact animals. Microscopic fields were randomly selected based on identifying well-structured astrocytes using astrocyte-specific anti-GFAP immunofluorescence. Subsequently, the number of Y chromosome positive astrocytes was counted, and a comparison made between the two hemispheres. In each of the three lesioned animals, more male donor marrow-derived astrocytes were detected on the ischemic side than on the non-ischemic side (FIG. 2). The increase in number of marrow-derived astrocytes in lesioned animals was 47% for experimental animal 1 (E1), 36% for experimental animal 2 (E2), and 14% for experimental animal 3 (E3). In intact rats, generally smaller differences in the number of marrow derived astrocytes between the two hemispheres were detected (5% for control 1, 21% for control 2).

1. Summary of Observations in Rats following Middle Cerebral Artery Occlusion
   a. Marrow-derived cells can be detected throughout the brains of transplanted rats, including in the ischemic parietal cortex.
   b. Marrow-derived astrocytes participate in the gliosis induced by MCA occlusion.
   c. More marrow-derived cells were detected in the ischemic cortex than in the contralateral non-ischemic cortex.
   d. More marrow-derived astrocytes were detected in the ischemic cortex than in the contralateral non-ischemic cortex.

2. General Conclusions from Rat Studies

Marrow-derived cells can be detected throughout the brains of female rats following transplantation with male bone marrow. Such cells are detectable in transplant recipients before and after brain injury. As we previously observed in mice, some marrow-derived cells differentiate into astrocytes. Such astrocytes participate in lesion-induced gliosis. Results with the acute MCA occlusion experiment show that there is some preferential association of marrow-derived cells, in particular astrocytes, with the region of gliosis. Preferential association of marrow-derived glia with regions of gliosis shows that these cells could be used as vehicles to deliver therapeutic genes to sites of CNS injury.

Experiment 10: Effect of Transplantation with Genetically Engineered Marrow Cells in a Mouse Model of Parkinson's Disease Mouse marrow was harvested and transduced with a retroviral vector as described. Cells were transduced with an MLV-based vector expressing rat glial cell line-derived neurotrophic factor (GDNF). This factor has been shown to provide neuroprotective effects in some rodent models of neurodegeneration. Six weeks after bone marrow transplantation, mice were treated with 1-methyl-4-phenyl-1,2,3,6-tetrahydropyridine (MPTP), a substance which gets metabolized within the brain into a potent neurotoxin specific for dopaminergic neurons. The significant neuron death in the substantia nigra resembles that seen in patients with Parkinson's disease. Using a device to measure the activity level of mice, the effect of the MPTP treatment on control and GDNF-transplanted mice was measured.

In the first 3 days, the overall horizontal activity and number of movements recorded increased in both the control and experimental groups (FIG. 3). Between 6 days and 2 weeks after MPTP treatment, the GDNF-treated group showed a less marked increase in number of movements than the control group. The level of horizontal activity also increased less in the mice transplanted with GDNF-treated marrow than in controls, although the difference between the groups was less marked than that seen in measurements of the number of movements. In these preliminary experiments, the number of animals is too small to assign statistical significance to the observed differences between control and experimental groups. However, they warrant the conclusion that marrow-derived cells migrating into the brain, when engineered to express neuroprotective growth factors such as GDNF, would protect brains of treated animals from experimentally induced neurodegeneration.

REFERENCES

1. Skoff, R. P. & Knapp, P. E. (1995) in *Neuroglia*, eds. Kettenmann, H. & Ransom, B. R. (Oxford University Press, New York), pp. 135–148.
2. Theele, D. P. & Streit, W. J. (1993) *Glia.* 7, 5–8.
3. Altman, J. (1994) *TINS* 17, 47–49.
4. Lewis, P. D. (1968) *Brain.* 91, 721–738.
5. Kitamura, T., Miyake, T. & Fujita, S. (1984) *J. Comp. Neurol.* 226, 421–433.
6. Neuhaus, J. & Fedoroff, S. (1994) *Glia.* 11, 11–17.
7. Perry, V. H. & Gordon, S. (1988) *TINS* 11, 273–278.
8. Ling, E. -A. & Wong, W. -C. (1993) *Glia.* 7, 9–18.
9. Perry, V. H. (1994) *Macrophages and the Nervous System* (R. G. Landes Company, Austin, Tex.),
10. Fedoroff, S. (1995) in *Neuroglia*, eds. Kettenmann, H. & Ransom, B. R. (Oxford University Press, New York), pp. 162–181.
11. Eglitis, M. A., Kantoff, P., Gilboa, E. & Anderson, W. F. (1985) *Science* 230, 1395–1398.
12. Bodine, D. M., Seidel, N., Karlsson, S. & Nienhuis, A. W. (1990) *Prog. Clin. Biol. Res.* 352, 287–299.
13. Luskey, B. D., Rosenblaft, M., Zsebo, K. & Williams, D. A. (1992) *Blood.* 80, 396–402.
14. Armentano, D., Yu, S. -F., Kantoff, P. W., von Ruden, T., Anderson, W. F. & Gilboa, E. (1987) *J. Virol.* 61, 1647–1650.
15. Russell, E. S. (1979) *Adv. Genet.* 20, 357–459.
16. Young, W. S., Mezey, E. & Siegel, R. E. (1986) *Brain. Res.* 387, 231–241.
17. Bradley, D. J., Towle, H. C. & Young, W. S. (1992) *J. Neurosci.* 12, 2288–2302.
18. Bishop, C. E., Boursot, P., Baron, B., Bonhomme, F. & Hatat, D. (1985) *Nature* 315, 70–72.
19. LeMoine, C. & Young, W. S. (1992) *Proc. Natl. Acad. Sci. U. S. A.* 89, 3285–3289.
20. Berghom, K. A., Bonnett, J. H. & Hoffman, G. E. (1994) *J. Histochem. Cytochem.* 42, 1635–1642.
21. Lawson, L. J., Perry, V. H., Dri, P. & Gordon, S. (1990) *Neurosci.* 39, 151–170.
22. Austyn, J. M. & Gordon, S. (1981) *Eur. J Immunol.* 11, 805–815.
23. Hsu, S. M., Raine, L. & Fanger, H. (1981) *J. Histochem. Cytochem.* 29, 577–580.
24. Smart, I. (1961) *J. Comp. Neurol.* 116, 325–347.
25. Altman, J. (1969) *J. Comp. Neurol.* 137, 433–458.
26. Sturrock, R. R. & Smart, I. H. M. (1980) *J. Anat.* 130, 391–415.
27. Alvarez-Buylla, A. & Lois, C. (1995) *Stem. Cells.* 13, 263–272.
28. Weiss, S., Reynolds, B. A., Vescovi, A. L., Morshead, C., Craig, C. G & van der Kooy, D. (1996) *TINS* 19, 387–393.
29. Chiang, C. S., McBride, W. H. & Withers, H. R. (1993) *Radiother. Oncol.* 29, 60–68.
30. Lillien, L. E. & Raff, M. C. (1990) *Neuron.* 5, 111–119.
31. Giulian, D. (1988) in *The Biochemical Pathology of Astrocytes*, Alan R. Liss, pp. 91–105.
32. Giulian, D., Chen, J., Ingeman, J. E., George, J. K. & Noponen, M. (1989) *J. Neurosci.* 9, 4416–4429.
33. Wilson, M. A. & Molliver, M. E. (1994) *Glia.* 11, 18–34.
34. Lindsay, R. M., Wiegand, S. J., Altar, C. A. & DiStefano, P. S. (1994) *Trends Neurosci.* 17, 182–190.
35. Verrall, M. (1994) *Nature* 370, 6.
36. Tamura A, Graham D I, McCulloch J, Teasdale G M (1981) *J. Cereb. Blood Flow Metabol.* 1: 53–60.

We claim:

1. A method of treating Parkinson's disease, comprising:
   transfecting harvested bone marrow cells with a retroviral vector comprising a gene for glial cell line-derived neurotrophic factor (GDNF);
   administering the transfected cells intravenously to a subject having Parkinson's disease; and
   allowing the transfected cells to migrate to the brain of the subject and express the GDNF gene, thereby treating the Parkinson's disease.

2. The method of claim 1, wherein the transfected cells differentiate into astroglia and microglia in the brain of the subject.

3. The method of claim 1, wherein the transfected cells migrate to the cortex, hippocampus, thalamus, brainstem or cerebellum of the brain.

4. The method of claim 1, further comprising culturing the harvested bone marrow in vitro in a cell culture medium comprising IL-3, IL-6, and stem cell factor prior to transfection with the GDNF gene.

5. The method of claim 4, wherein the harvested bone marrow is cultured in vitro for 48 hours.

6. The method of claim 1, wherein the subject has been sub-lethally irradiated prior to administration of the transfected cells.

7. The method of claim 1, wherein the retroviral vector is a Moloney murine leukemia virus vector.

8. A method of treating Parkinson's disease, comprising:
   culturing harvested bone marrow cells in a cell culture medium comprising IL-3, IL-6, and stem cell factor;
   transfecting the harvested bone marrow cells with a Moloney murine leukemia virus vector comprising a gene for glial cell line-derived neurotrophic factor (GDNF);
   administering the transfected cells intravenously to a subject having Parkinson's disease; and
   allowing the transfected cells to migrate to the brain of the subject and express the GDNF gene, thereby treating the Parkinson's disease.

* * * * *